(12) United States Patent
Bienkiewicz

(10) Patent No.: US 10,449,213 B2
(45) Date of Patent: Oct. 22, 2019

(54) COMBINATORIAL APPROACH TO TREATING ALZHEIMER'S DISEASE

(71) Applicant: Florida State University Research Foundation, Inc., Tallahassee, FL (US)

(72) Inventor: Ewa Anna Bienkiewicz, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/194,704

(22) Filed: Jun. 28, 2016

(65) Prior Publication Data

US 2016/0303160 A1    Oct. 20, 2016

Related U.S. Application Data

(63) Continuation-in-part of application No. 14/539,515, filed as application No. PCT/US2012/050582 on Aug. 13, 2012, which is a continuation-in-part of application No. 14/237,216, filed as application No. PCT/US2012/050582 on Aug. 13, 2012.

(60) Provisional application No. 61/522,759, filed on Aug. 12, 2011, provisional application No. 61/903,535, filed on Nov. 13, 2013.

(51) Int. Cl.
| | |
|---|---|
| *A61K 31/714* | (2006.01) |
| *A61K 31/4045* | (2006.01) |
| *A61K 31/05* | (2006.01) |
| *A61K 31/353* | (2006.01) |
| *A61P 25/28* | (2006.01) |
| *A61P 39/06* | (2006.01) |
| *A61K 9/00* | (2006.01) |

(52) U.S. Cl.
CPC .......... *A61K 31/714* (2013.01); *A61K 9/0014* (2013.01); *A61K 9/0019* (2013.01); *A61K 31/05* (2013.01); *A61K 31/353* (2013.01); *A61K 31/4045* (2013.01); *A61P 25/28* (2018.01); *A61P 39/06* (2018.01)

(58) Field of Classification Search
None
See application file for complete search history.

(56) References Cited

U.S. PATENT DOCUMENTS

| 5,958,964 A | 9/1999 | Pappolla | |
|---|---|---|---|
| 6,008,221 A | 12/1999 | Smith et al. | |
| 2005/0019330 A1 | 1/2005 | Schenk | |
| 2005/0031651 A1 | 2/2005 | Gervais et al. | |
| 2005/0164911 A1* | 7/2005 | Cavalieri | A61K 31/05 |
| | | | 514/613 |
| 2006/0148727 A1* | 7/2006 | Hendrix | A61K 31/198 |
| | | | 514/27 |
| 2006/0257502 A1* | 11/2006 | Liu | A23L 33/15 |
| | | | 424/682 |
| 2007/0219171 A1* | 9/2007 | Lulla | A61K 9/12 |
| | | | 514/177 |
| 2007/0298133 A1* | 12/2007 | Velazquez | A61K 31/353 |
| | | | 424/729 |
| 2015/0065449 A1* | 3/2015 | Bienkiewicz | A61K 31/714 |
| | | | 514/52 |

FOREIGN PATENT DOCUMENTS

| WO | 0012102 | 3/2000 |
|---|---|---|
| WO | 0203074 | 1/2002 |
| WO | 0205813 | 1/2002 |

OTHER PUBLICATIONS

Vitiello et al., "Sleep Disturbances in Patients with Alzheimer's Disease Epidemiology, Pathophysiology and Treatment" CNS drugs (2001) vol. 15 No. 10 pp. 777-796 (Year: 2001).*
Wolters et al., "Cobalamin: a critical vitamin in the elderly" Preventative Medicine (2004) vol. 39 pp. 1256-1266 (Year: 2004).*
Kwon et al., "Melatonin Potentiates the Neuroprotective Properties of Resveratrol Against Beta-Amyloid-Induced Neurodegeneration by Modulating AMP-Activated Protein Kinase Pathways" Journal of Clinical Neurology (2010) vol. 6 pp. 127-137 (Year: 2010).*
Riemersama-van der Lek et al., "Effect of Bright Light and Melatonin on Cognitive and Noncognitive Function in Elderly Residents of Group Care Facilities a Randomized Controlled Trial" JAMA vol. 299 No. 2 pp. 2642-2655 (Year: 2008).*
Cardinali e al., "The Use of Chronobiotics in the Resynchronization of the Sleep/Wake Cycle. Therapeutical Application in the Early Phases of Alzheimer's Disease" Recent Patents on Endocrine, Metabolic & Immune Drug Discovery vol. 5 pp. 80-90 (Year: 2011).*
Levites et al., "Neuroprotection and neurorescue against Aβ toxicity and PKC-dependent release of non-amyloidogenic soluble precursor protein by green tea polyphenol (-)-epigallocatechin-3-gallate" FASEB Journal vol. 17 issue 8. pp. 952-954 (Year: 2003).*

(Continued)

*Primary Examiner* — Eric Olson
(74) *Attorney, Agent, or Firm* — Christopher M. Ramsey; GrayRobinson, P.A.

(57) ABSTRACT

A therapeutically effective composition for treating Alzheimer's disease includes a pharmaceutically acceptable dosage form comprising melatonin, resveratrol, EGCG, and vitamin B12 combined in a therapeutically effective amount. A combinatorial treatment method for Alzheimer's disease includes administering to a human having Alzheimer's disease a therapeutically effective combination of melatonin, resveratrol, EGCG, and vitamin B12. A method of treating Alzheimer's disease includes administering to a human having Alzheimer's disease a therapeutically effective amount of a pharmaceutically acceptable dosage form comprising melatonin, resveratrol, EGCG, and vitamin B12.

6 Claims, 7 Drawing Sheets
Specification includes a Sequence Listing.

(56) References Cited

OTHER PUBLICATIONS

Lambert et al., "Transdermal delivery of (---)-epigallocatechin-3-gallate, a green tea polyphenol, in mice" Journal of Pharamcy and Pharmacology vol. 58 pp. 599-604 (Year: 2006).*
Yang et al., "Effects of Chemical and Physical Enhancement Techniques on Transdermal Delivery of Cyanocobalamin (Vitamin B12 ) In Vitro" Pharmaceutics vol. 3 pp. 474-484 (Year: 2011).*
Lemon et al., "A Dietary Supplement Abolishes Age-Related Cognitive Decline in Transgenic Mice Expressing Elevated Free Radical Processes" Exp Biol Med vol. 228 pp. 800-810 (Year: 2003).*
ABC News; "Combining Drugs Doesn't Improve Arterial Disease Outcome"; Ed Edelson, Healthday Reporter; Mar. 23, 2016; http://abcnews.go.com/health/heathday/story.
Bett et al., Activity Relationships in Peptide Modulators of B-Amyloid Protein Aggreation; Variation in a, a-Disubstitution Results in Altered Aggregate Size and Morphology, ACCS Chem, Neurosci, (2010), pp. 608-626.
Flicker et al., B-Vitamins Reduce Plasma Levels of Beta Amyloid; Neurobiol Aging, Feb. 2008, 29(2); pp. 303-305. Abstract.
Fuso et al., "B-Vitamin Deprivation INduces Hyperhomocysteinemia and Brain S-Adenosylhomocysteine, Depletes Brain S-Adenosylmethionine, and Enhances PS1 and BACE Expression and Amyloid-B Deposition in Mice, Mol. Cell leurosci," 37 (2008) pp. 731-746.
Guo et al.; Journal of Alzheimer's Disease: JAD vol. 19, No. 4, pp. 1359-1370; 2010.
Karin Nilsson, Lars Gustafson, Bjorn Hultberg; "Elevated Plasma Homocysteine Level in Vascular Dementia Reflects the Vascular Disease Process"; Dementia and Geriatric Cognitive Disorders; Feb. 16, 2013; 3; pp. 16-24.
Ning Yin, Wenzhe Ma, Jianfeng Pei, Qi Ouyang, Chao Tang, Luhua Lai; "Synergistic and Antagonistic Drug Combinations Depend on Network Topology," PLOS ONE, Apr. 2014; vol. 9; Issue 4.
Refsum et al., Low Vitamin B-12 Status in Confirmed Alzheimer's Disease as Revealed by Serum Holotranscobalamin; J Neurol Neurosurg Psychiatry, 2003, 74; pp. 959-961.
Silvia Lopez-Burillo, Dun-Xian Tan, Jaun C Mayo, Rosa M Sainz, Lucien C Manchester, Russel J Reiter; "Melatonin, Xanthurenic Acid, Resveratrol, EGCG, Vitamin C and x-lipoic Acid Differentially Reduce Oxidative DNA Damage Induced by Fenton Reagents: a Study of Their Individual and Synergistic Actions"; Journal of Pineal Research, 2003; 34; pp. 269-277.
The Warfarin Antiplatelet Vascular Evaluation Trial Investigators; "Oral Anticoagulant and Antiplatelet Therapy and Peripheral Arterial Disease"; The New England Journal of Medicine, Jul. 19, 2007; vol. 357, No. 3; pp. 217-227.
Walter Ling, Steven Shoptow, Maureen Hillhouse, Michelle A. Bholat, Charles Charuvastra, Keith Heinzerling, David Chim, Jeffrey Annon, Patrick T. Dowling, Geetha Joraimani; "Double-Blind Placebo-Controlled Evaluation of the Prometa Protocol for Methamphetamine Dependence"; Society for the Study of Addiction, 2011; Addiction, 107, pp. 361-369.
Zhang et al., Hyperhomocysteinemia Increases B-Amyloid by Enhancing Expression of y-Secretase and Phosphorylation of Amyloid Percursor Protein in Rat Brain, The American Journal of Pathology, vol. 174, No. 4; Apr. 2009; pp. 1481-1491.
Bush, A.I.; "The Metal Theory of Alzheimer's Disease"; Journal of Alzheimer's Disease, vol. 33; pp. S277-S281; 2013.
Cristovao et al.; "Metals and Neuronal Metal Binding Proteins Implicated in Alzheimer's Disease"; Oxidative Medicine and Cellular Longevity; 2016.
Huang et al; "Redox-Active Metals, Oxidative Stress, and Alzheimer's Disease Pathology"; Redox-Active Metals in Neurological Disorders; vol. 1012; pp. 153-163; 2004.
Lipinski, B.; "Hydroxyl Radical and Its Scavengers in Health and Disease"; Oxidative Medicine and Cellular Longevity; 2011.
McCleery et al.; "Pharmacotherapies for Sleep Disturbances in Alzheimer's Disease"; Cochrane Database of Systematic Reviews; Issue 3; Art No. CD009178; 2014.
Singer et al.; "A Multicenter, Placebo-Controlled Trial of Melatonin for Sleep Disturbance in Alzheimer's Disease"; Sleep, vol. 26(7); pp. 893-901; Nov. 1, 2003.
Chuanhai Cao et al.; "The Potential Therapeutic Effects of THC on Alzheimer's Disease"; Journal of Alzheimer's Disease, vol. 42, pp. 973-984; 2014.
Ed Edelsonhealthday; "Combining Drugs Doesn't Improve Arterial Disease Outcome"; p://abcnews.go.com/Healthy?Healthday/story?id=4507980; Mar. 23, 2014.
Elisabeth Lawler et al.; "Alzheimer Disease: Monotherapy vs. Combination Therapy"; American Family Physician; vol. 95(7); p. 452; Apr. 1, 2017.
Gary W. Arendash et al.; "Caffeine Reverses Cognitive Impairment and Decreases Brain Amyloid-Beta Levels in Alzheimer's Disease Mice"; Journal of Alzheimer's Disease; vol. 17; pp. 661-680; 2009.
Gopal Thinakaran et al.; "Metabolism of the "Swedish" Amyloid Precursor Protein Varian in Neuro2a (N2a) Cells"; The Journal of Biological Chemistry; vol. 271, No. 16; pp. 9390-9397; Apr. 19, 1996.
Hilkka Soininen et al.; "24-month Intervention With a Specific Multinutrient in People with Prodromal Alzheimer's Disease (LipidiDiet): a Randomised, Double-Blind, Controlled Trial"; www.thelancet.com/neurology; vol. 16; pp. 965-975; Dec. 2017.
James A. Hendrix et al.; "Challenges, Solutions, and Recommendations for Alzheimer's Disease Combination Therapy"; Alzheimer's and Dementia Association; vol. 12; pp. 623-630; 2016.
Jeffrey L. Cummings et al.; "Treatment Combinations for Alzheimer's Disease: Current and Future Pharmacotherapy Options"; Journal of Alzheimer's Disease; vol. 67, pp. 779-794; 2019.
Jin Liu et al.; "Complex Brain Network Analysis and Its Applications to Brain Disorders: A Survey"; Hindawi Complexity; Article ID 8362741; pp. 1-28; 2017.
K. Rajasekhar et al.; "Current Progress, Challenges and Further Prospects of Diagnostic and Therapeutic Interventions in Alzheimer's Disease"; Royal Society of Chemistry; vol. 8; pp. 23780-23804; 2018.
Kelvin K.F. Tsoi et al.; "Monotherapy is Good Enough for Patients with Mild-to Moderate Alzheimer's Disease: A Network Meta-Analysis of 76 Randomized Controlled Trials"; Clinical Pharmacology and Therapeutics; vol. 105, No. 1; Jan. 2019.
Natasa Dragicevic et al.; "Melatonin Treatment Restores Mitochondrial Function in Alzheimer's Mice: A Mitochondrial Protective Role of Melatonin Membrane Receptor Signaling"; Journal of Pineal Research; vol., 51; pp. 75-86; 2011.
Ning Yin et al.; "Synergistic and Antagonistic Drug Combinations Depend on Network Topology"; PLOS ONE, vol. 9, Issue 4; Apr. 2014.
R. Anand et al.; "Therapeutics of Alzheimer's Disease: Past, Present and Future"; Neuropharmacology, vol. 76, pp. 27-50; 2014.
The New England Journal of Medicine; "Oral Anticoagulant and Antiplatelet Therapy and Peripheral Arterial Disease"; vol. 357, No. 3; Jul. 19, 2007.
Walter Ling et al.; "Double-Blind Placebo-Controlled Evaluation of the Prometa Protocol for Methamphetamine Dependence"; National Institutes of Health; vol. 107(2); pp. 361-369; Feb. 2012.
William O. Pickrell et al.; "New Treatments in Alzheimer's Disease"; Journal of Neurology; vol. 265; pp. 2162-2163; Aug. 21, 2018.
Yadong Huang et al.; "Alzheimer Mechanisms and Therapeutic Strategies"; Cell; pp. 1204-1222; Mar. 16, 2012.
Yi Tang et al.; "A Systems-Based Model of Alzheimer's Disease"; Alzheimer's and Dementia Association; vol. 15; pp. 168-171; 2019.

* cited by examiner

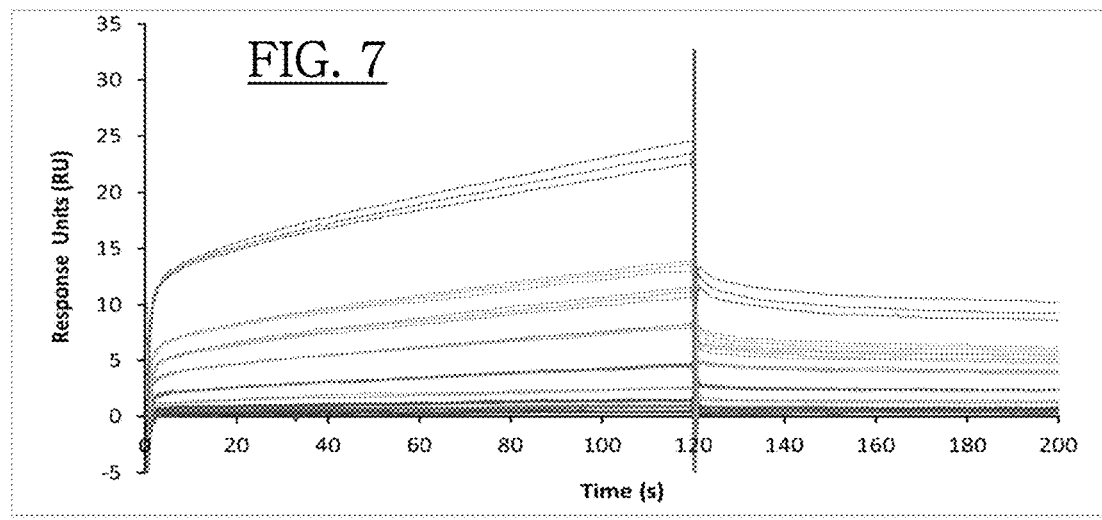
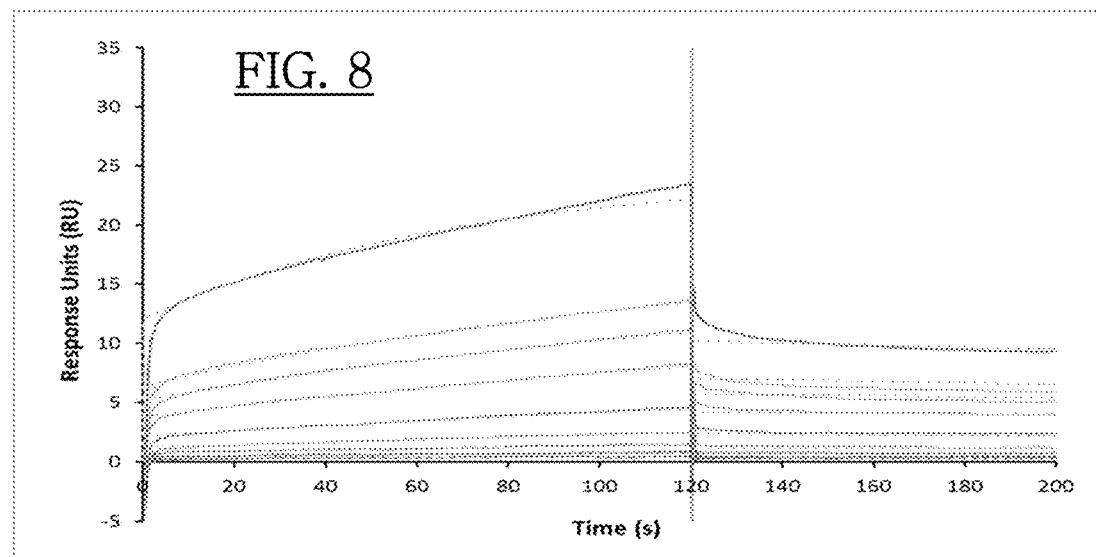

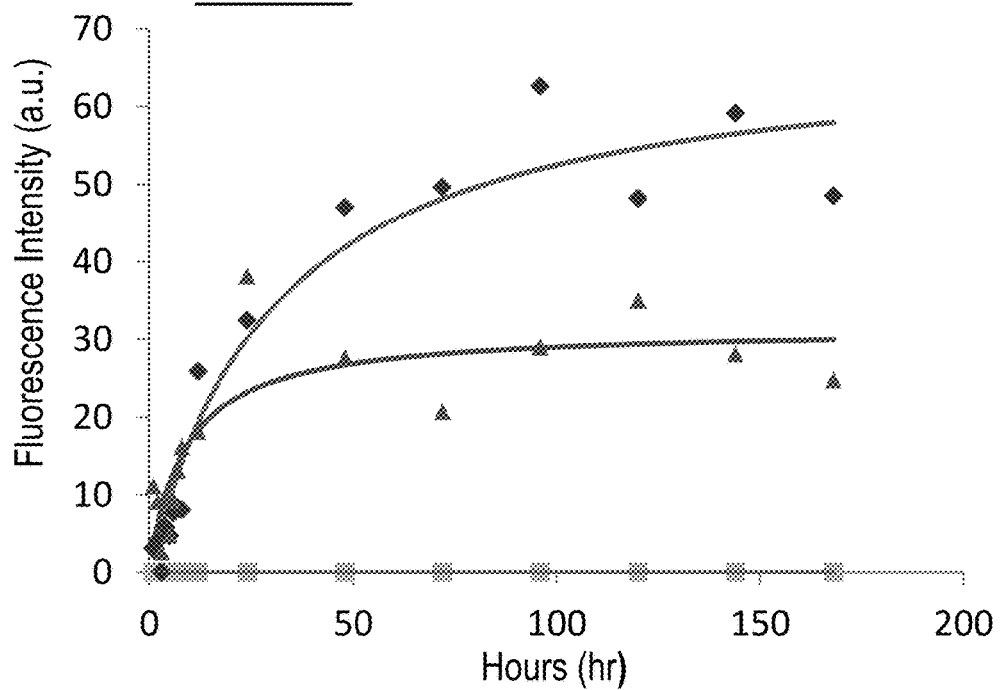
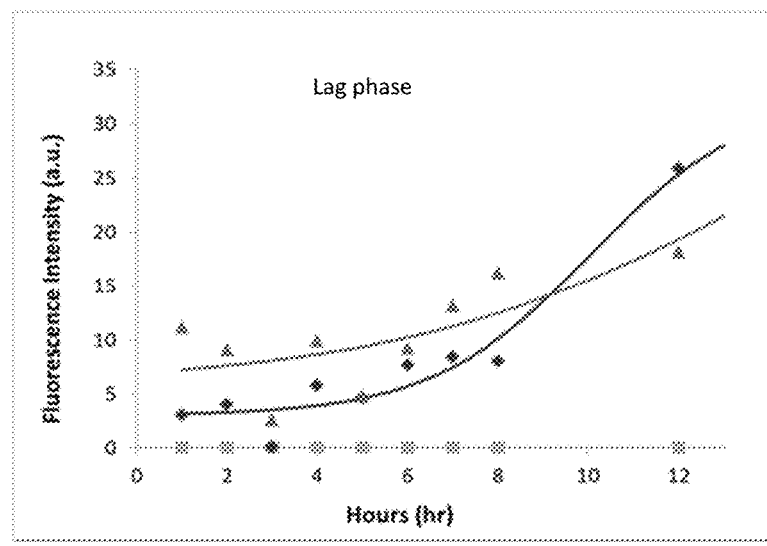

FIG. 13

COMBINATORIAL APPROACH TO TREATING ALZHEIMER'S DISEASE

CROSS-REFERENCE TO RELATED APPLICATIONS

This is a continuation-in-part of U.S. patent application Ser. No. 14/539,515, filed Nov. 12, 2014, which claims the benefit U.S. provisional Application No. 61/903,535, filed Nov. 13, 2013 and is a continuation-in-part of U.S. patent application Ser. No. 14/237,216, filed Feb. 5, 2014, which is a National Stage application of PCT/US2012/050582, filed Aug. 13, 2012, which claims the benefit of U.S. provisional Application No. 61/522,759, filed Aug. 12, 2011. The entire contents of these prior documents are hereby incorporated by reference.

FIELD

This disclosure relates to the field of treatment of amyloidoses. More particularly, it relates to treating conditions associate with amyloid-beta peptide aggregation.

SEQUENCE LISTING

This disclosure includes a Sequence Listing electronically submitted via EFS-web to the United States Patent and Trademark Office as a text file named "Sequence_Listing.txt." The electronically filed Sequence Listing serves as both the paper copy required by 37 C.F.R. § 1.821(c) and the computer readable file required by 37 C.F.R. § 1.821(c). The information contained in the Sequence Listing is incorporated herein by reference in its entirety.

BACKGROUND

Amyloidoses are pathological conditions characterized by the aggregation of certain proteins into harmful oligomers and deposits called amyloid fibrils. These self-associated amyloid species are toxic to various types of cells, including certain type of brain cells. A particularly prominent example of an amyloidosis is Alzheimer's disease. In Alzheimer's disease, amyloid oligomers and fibrils accumulate in the brain, deteriorating the brain's memory functions.

The amyloid oligomers and fibril deposits in the brain of a patient with Alzheimer's disease are formed from a particular peptide called amyloid-beta peptide. Amyloid-beta peptide, which is also referred to as "Aβ", is a protein of about 40-43 amino acid residues. Its 40 amino acid form (Aβ 1-40), 42 amino acid form (Aβ1-42), and 43 amino acid form (Aβ1-43) have been associated with amyloid oligomer formation and fibril deposits. Amyloid-beta peptide is the major constituent of neuritic plaque deposits, which are distributed throughout the walls of cerebral blood vessels and the neuropil of the central nervous system.

Approximately five million Americans are currently afflicted with Alzheimer's disease ("AD"), with a new case identified every 70 seconds. The AD diagnosis places each patient on an irrevocable path of fatal neurodegeneration, as there is currently no effective cure for this devastating disease. At present, the treatment options for Alzheimer's disease include cholinesterase inhibitor-type and receptor agonist-type drugs. These drugs help somewhat, but are not fully effective.

SUMMARY

A therapeutically effective composition for treating Alzheimer's disease includes a pharmaceutically acceptable dosage form comprising melatonin, resveratrol, EGCG, and vitamin B12 combined in a therapeutically effective amount. A combinatorial treatment method for Alzheimer's disease includes administering to a human having Alzheimer's disease a therapeutically effective combination of melatonin, resveratrol, EGCG, and vitamin B12. A method of treating Alzheimer's disease includes administering to a human having Alzheimer's disease a therapeutically effective amount of a pharmaceutically acceptable dosage form comprising melatonin, resveratrol, EGCG, and vitamin B12.

BRIEF DESCRIPTION OF THE DRAWINGS

FIG. 7 is a surface plasmon resonance (SPR) kinetic sensorgram of amyloid-beta in the presence of different concentrations of vitamin B12;

FIG. 8 is calculated fit of the SPR data of FIG. 7 using a 1:1 (B12:Aβ) binding model;

FIG. 9 is a graph of the fluorescence intensity of Thioflavin T in samples containing amyloid-beta peptide and vitamin B12, in which the amyloid-beta peptide was incubated in the presence of vitamin B12(■), absence of vitamin B12 (♦), and in which the amyloid fibrils formed in the experiments represented by ♦ were subsequently treated with vitamin B12 (▲);

FIG. 10 is a graph of the lag phase of the samples of FIG. 9;

FIG. 13 is a table of statistical p-values from experimental testing of different combinations of resveratrol (R), melatonin (M), EGCG (E), and B12 (B).

DETAILED DESCRIPTION

Figure 1:
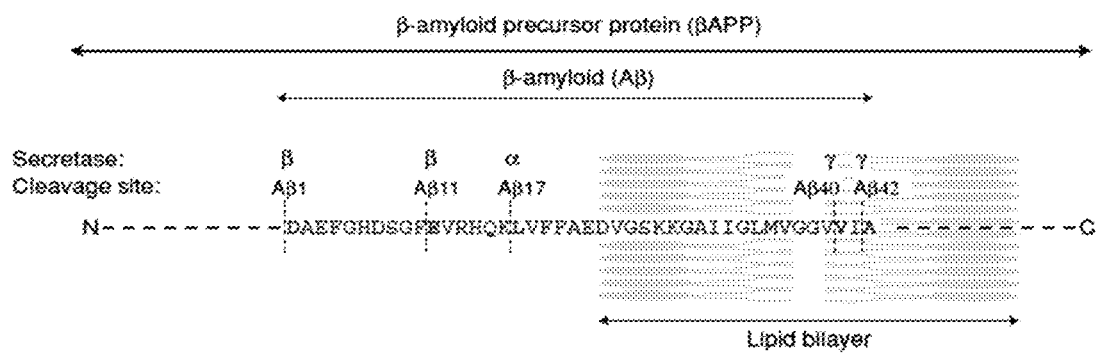
FIG. 1 is a diagram illustrating the location, sequence, and structure of the amyloid-beta peptide along the β-amyloid precursor protein (βAPP)

As mentioned above, one of the key components to blame for the pathology of Alzheimer's disease is the amyloid-beta (Aβ) peptide. Referring to FIG. 1, the amyloid-beta peptide is a fragment of the beta-amyloid precursor protein (βAPP). When βAPP is cleaved, it releases the 40-42 amino acid fragment amyloid-beta peptide.

Figure 2:
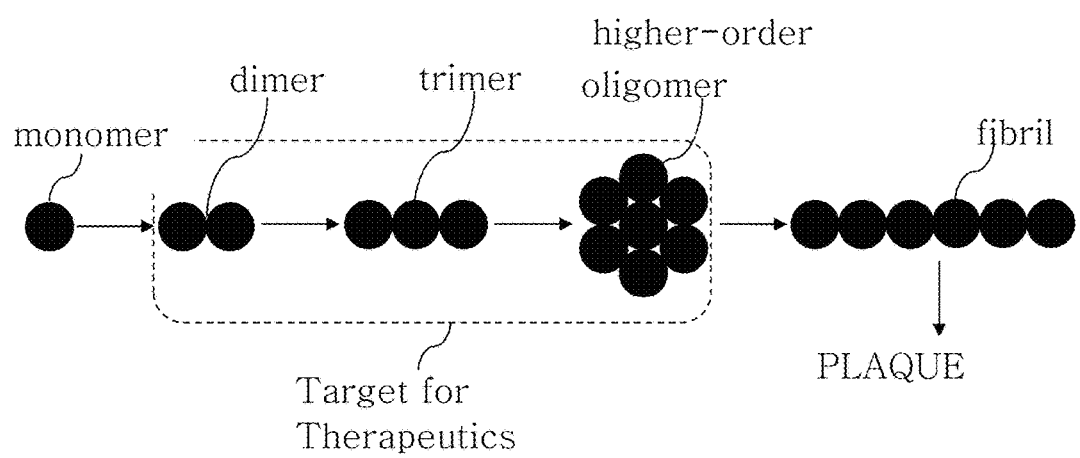
FIG. 2 is a diagram illustrating the various degrees of agglomeration of amyloid-beta peptide from monomer to plaque.

With reference now to FIG. 2, amyloid-beta peptide monomers have an ability to self-associate or aggregate into higher-order oligomeric structures (dimers, trimers, etc.), fibrils, and plaques. Recent evidence shows that the amyloid-beta peptide's structural diversity translates into variations in its neurotoxicity, with the dimeric/oligomeric states shown to be the most harmful, and the monomeric form thought to be neuroprotective.

Vitamin B deficiency has been implicated in processes affecting the progression of Alzheimer's-like pathology through (1) abnormal phosphorylation of the tau protein and formation of neurofibrillary tangles (Nicolia, et al, *Journal of Alzheimers Disease*, Vol. 19(3), pages 895-907 (2010)), (2) increased production of the amyloid-beta peptide (Fuso, et al, *Molecular and Cellular Neuroscience*, Vol. 37(4), pages 731-746 (2008)), and (3) increased self-association of the amyloid-β peptide leading to neurotoxicity (described here). It is plausible that the therapeutic effects of vitamin B12 for AD and AD-like pathologies may include these three pathways in concert.

Although the mechanisms underlying these phenomena require further investigation, it is clear that any factors that modify amyloid-beta peptide self-association are likely to influence the survival of neuronal cells. In this context, I hypothesized that directly binding small molecules to the various structural forms of the amyloid-beta peptide may be an effective way shift the relative distribution of the amyloid-beta structures away from the toxic oligomers, fibrils, and plaques toward the monomer form.

Numerous clinical investigations have demonstrated that vitamin B12 is crucial for maintaining cognitive function. Patients exhibiting Alzheimer's-like pathology display a marked decrease in vitamin B12 levels. This observation implies a "loss of function" scenario, where tasks normally carried out by vitamin B12 are attenuated. Although vitamin B12 is known for its function as a co-factor in metabolic reactions and DNA synthesis, I hypothesized that vitamin B12 may also play a direct role in modulating the levels of toxic amyloid-beta aggregates. As a "small molecule", I suspected that vitamin B12 could carry out this task by directly interacting with the amyloid-beta peptide, thereby modulating its ability to self-assemble and reducing its toxicity. The experimental results presented here demonstrate that vitamin B12 influences both the conformational state adopted by the amyloid-beta peptide and the extent of neuronal cell death triggered by its presence.

Using a multidisciplinary approach, combining biophysical and neuronal-cell culture studies, it is shown that vitamin B12 is a neuroprotective binding partner of the amyloid-beta peptide. This indicates that B12 plays a preventive role in the process of self-association and formation of toxic amyloid-beta peptide aggregates that have been demonstrated to be an integral part of the AD pathology.

These findings are consistent with clinical observations where diminished levels of vitamin B12 were observed to accompany the progression of Alzheimer's disease. They also point to vitamin B12's utility as a therapeutic agent that alleviates neuronal-cell death by modulating Aβ peptide aggregation and formation of toxic species. The efficacy of treatment by vitamin B12 may be enhanced by utilizing targeted delivery of vitamin B12 to the brain, bypassing the gut, and/or by derivatization of the vitamin B12 molecule.

At the outset, it should be understood that the term "vitamin B12" as used herein refers to the compound cobalamin and its natural and synthetic derivatives, which include, but are not limited to, cyanocobalamin, methylcobalamin, adenosylcobalamin, and hydroxycobalamin.

Remarkably, the results discussed in the Examples section show that vitamin B12 causes amyloid-beta peptide monomers to dissociate from the higher-order structural form of amyloid-beta peptides. These higher-order structural forms (dimers, trimers, higher-order oligomers, fibrils, etc.) are referred to herein as amyloid-beta peptide aggregates because they contain a plurality of aggregated amyloid-beta peptide monomers.

In a first method aspect, a method of treating amyloid-beta peptide aggregation in a patient having Alzheimer's disease includes determining a first level of amyloid-beta peptides in the patient, establishing a first dose of vitamin B12 based on the first level of amyloid-beta peptides in the patient, the first dose being sufficient to promote dissociation of amyloid-beta peptide monomers from the amyloid-beta peptide aggregates in the patient, and administering the first dose to the patient.

This method may form part of a treatment regimen in which the steps are repeated multiple times and the dosage of vitamin B12 in each subsequent dose is adjusted according to the level of amyloid-beta peptide aggregates remaining in the patient after the previous dose. In this case, the method further comprises determining a second level of amyloid-beta peptides in the patient, establishing a second dose of vitamin B12 based on the second level of amyloid-beta peptides in the patient, and administering the second dose to the patient.

In another method aspect, a method of treating Alzheimer's disease includes administering an effective amount of vitamin B12 to a patient, the effective amount being sufficient to cause dissociation of amyloid-beta peptide monomers from pre-existing amyloid-beta peptide oligomers in the patient, the effective amount being based on a predetermined quantity of amyloid-beta peptide oligomers in the patient.

In another method aspect, a method of preventing neuronal-cell death includes estimating a level of amyloid-beta peptides in a subject, establishing an effective amount of vitamin B12 based on the estimated level, and administering the effective amount of vitamin B12 to the subject. This method is particularly useful at preventing the death of hippocampal cells.

In another method aspect, a method of treating amyloid-beta peptide aggregation in a subject comprises contacting at least one amyloid-beta peptide oligomer formed from a plurality of amyloid-beta peptide monomers with an effective amount of vitamin B12, the effective amount being sufficient to stimulate dissociation of the amyloid-beta peptide monomers from the amyloid-beta peptide oligomer.

The level of amyloid-beta peptides in the patient may be determined by extracting a plasma sample from the patient and measuring the quantity of amyloid-beta peptide in the sample. Suitable techniques for measuring the quantity of amyloid-beta peptides in the sample already exist. Some examples of these techniques are now described.

One technique for measuring the quantity of amyloid-beta peptide in a sample employs a sandwich Enzyme-Linked Immunosorbent Assay, or ELISA, methodology. Typically, ELISA utilizes a system with two antibodies. One is immobilized on a surface (capture antibody) and serves to recognize and bind an antigen, in this case the amyloid-beta peptide. The second antibody (detection antibody) recognizes the same antigen (the amyloid-beta peptide) and is conjugated to a system that allows for detection (signal amplification) of the original capture antibody/amyloid-beta peptide complex. An example of the detection system is horse radish peroxidase (HRP) and alkaline phosphatase (ALP), where an enzymatic reaction leads to a change in color (detection/signal amplification) in the presence of the antigen-antibody complex. In a standard protocol, the major steps include: (1) application of sample onto a surface with the capture antibody, (2) washing off the unbound material, (3) applying the second (detection) antibody, (4) washing off unbound material, and (5) executing of a reaction/protocol that allows for detection and quantitation of the antigen. A standard curve generated using known concentrations of the antigen (amyloid-beta peptide) is used to interpolate the concentration of the antigen of interest in the respective sample. ELISA kits for detection of various isoforms of the amyloid-beta peptide are available from several vendors. Examples include: BETAMARK® Beta-Amyloid x-42; Chemiluminescent ELISA Kit, Covance, Catalog Number: SIG-38952 (detects amyloid-beta x-42); BETAMARK® Total Beta-Amyloid; Chemiluminescent ELISA Kit, Covance, Catalog Number: SIG-38966 (detects amyloid-beta 1-38, 1-40, 1-42, and 1-46 of amyloid-beta peptide; Human Amyloidβ(1-x) Assay Kits, Immuno-Biological Laboratories Co., Ltd. (detect Aβ(1-40), Aβ(1-42) and Aβ(N3pE-42) separately in plasma, cerebrospinal fluids, and serum); and ABtest for quantitative determination of beta-amyloid pool in blood, Araclon Biotech, (detects 1-40 and 1-42 isoforms of amyloid-beta found in free plasma and bound to other plasma components, including lipids and proteins, and to blood cells).

The hippocampal cell culture results show that, when the ratio of vitamin B12 to amyloid-beta peptide is approximately 1:1, optimum effectiveness is achieved. Administering an excess of vitamin B12 does not appear to enhance the amount of amyloid-beta peptide monomers dissociated from the amyloid-beta peptide aggregates, but administering less vitamin B12 diminishes the amount of amyloid-beta peptide monomers dissociated from the amyloid-beta peptide aggregates.

A dose of vitamin B12 may be, in some scenarios, at least equimolar with the molarity of amyloid-beta peptide in the patient estimated from the plasma sample. In the treatment regimen, the amount of vitamin B12 in each subsequent dose is adjusted according to the level of amyloid-beta peptide aggregates estimated to be in the patient after a previous dose.

The effective amount of vitamin B12 may be adapted to provide an approximately 1:1 ratio of vitamin B12 to amyloid-beta peptide in the patient. Accordingly, an exemplary effective amount is at least equimolar with the molarity of amyloid-beta peptide in the patient, as estimated from the sample. Another exemplary effective amount of vitamin B12 is at least one molecule of vitamin B12 per amyloid-beta peptide monomer dissociated from the amyloid-beta peptide oligomer.

The amount or quantity of amyloid-beta peptides in the subject may be extrapolated to account for the estimated total volume of the fluid tested in the subject. For example, the amount of amyloid-beta peptide in the subject's plasma is estimated by determining the quantity of amyloid-beta peptides in a known volume of the sample and extrapolating this quantity to correspond to the total amount of plasma in the subject. The total amount of plasma in the subject can be estimated from the volume of blood in the subject. The same technique is useful for estimating the amount of amyloid-beta peptides in the other embodiments described herein.

Vitamin B12 may be administered as an active ingredient in a pharmaceutical composition prepared to form a pharmaceutically acceptable dosage form. Pharmaceutically acceptable dosage forms include suspensions, tablets, capsules, injectables, transdermals, or the like that can be administered to a human or animal patient.

Exemplary ingredients in the composition include one or more excipients, diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

Vitamin B12 may be included in a pharmaceutical composition having one or more additional active ingredients. Examples of these additional active ingredients include, but are not limited to caffeine, resveratrol, melatonin, vitamin B6, epigallocatechin-3-gallate (EGCG), and folic acid.

A therapeutically effective composition for treating Alzheimer's disease includes a pharmaceutically acceptable dosage form comprising melatonin, resveratrol, EGCG, and vitamin B12. Additional compounds including, but not limited to, caffeine, nicotine, curcumin, steroids, folic acid, and vitamin D or any of the analogs of these compounds may optionally be included.

Individually, B12, melatonin, resveratrol, and EGCG target distinct, yet complementary aspects of amyloid beta peptide pathology. B12 performs the function discussed herein. Melatonin diminishes the formation of toxic amyloid-beta species, has anti-inflammatory properties, and impedes the abnormal phosphorylation of tau and neurofibrillary tangles. Resveratrol is an antioxidant that affects processes leading to diminished production of toxic amyloid-beta species. EGCG is a green tea extract that reduces amyloid-beta levels and modulates aggregation/toxicity of the amyloid-beta peptide.

The composition targets respective causative factors of amyloid-beta peptide pathology and is particularly preferred to treat Alzheimer's disease. In addition to their individual, unique modes of action targeting various cellular pathways, a number of the components may impede formation of toxic amyloid-beta species. This redundancy may be advantageous. Since the compounds target different aspects of the amyloid-beta peptide pathology, they function via different mechanisms, or bind to distinct regions of the peptide, thus acting in a complementary fashion.

There are many conventional techniques for administering the composition to patient. These administration techniques include, but are not limited to administering one or more pharmaceutically acceptable dosage forms such as a suspensions, tablets, suppositories, capsules, injectables, transdermals or the like that can be administered to a human or animal patient.

Other suitable administration techniques include oral, sublingual, buccal, intravenous, subcutaneous, transcutaneous, intramuscular, intracutaneous, intrathecal, epidural, intraocular, intracranial, inhalation, intranasal, or the like. Any combination of these administration techniques may also be used.

The composition may be administered in such a way that it reaches the target area of the body without passing through the gastrointestinal tract. This is because the GI tract can diminish the bioavailability of the compounds. One way to achieve this is by administering the composition topically or transdermally by applying it to the patient's skin, such as by using a transdermal patch, spraying onto the skin, applying a cream, or the like. Another way is by a direct brain-targeted delivery system, such as an injection or nasal delivery.

For a topical or injectable dosage form containing the melatonin, resveratrol, EGCG, and vitamin B12, these ingredients may be contained in a common solution or suspension. The solution may contain one or more pharmaceutically acceptable solvents, surfactants, and/or emulsifiers suitable for getting these ingredients into the solution.

In the composition of melatonin, resveratrol, EGCG, and vitamin B12, the therapeutically effective amount is an amount effective to achieve a desired therapeutic benefit, such as an amount effective to prevent, alleviate, ameliorate, or treat the underlying causes and/or symptoms of the physiological condition being treated.

For some uses of the composition, the therapeutically effective amount is an amount effective to modulate or ameliorate the symptoms of Alzheimer's disease or decrease the rate of advancement of Alzheimer's disease.

In humans, a therapeutically effective amount range is often 1-1,000 mg/day, including 1-25 mg/day, 25-50 mg/day, 50-75 mg/day, 75-100 mg/day, 100-150 mg/day, 150-200 mg/day, 200-250 mg/day, 250-300 mg/day, 300-350 mg/day, 350-400 mg/day, 400-450 mg/day, 450-500 mg/day, 500-550 mg/day, 550-600 mg/day, 600-650 mg/day, 650-700 mg/day, 700-750 mg/day, 750-800 mg/day, 800-850 mg/day, 850-900 mg/day, 900-950 mg/day, 950-1,000 mg/day. Higher doses (1,000-3,000 mg/day) might also be effective. The weight in mg is often calibrated to the body weight of the subject in kg, thus these example doses may also be written in terms of mg/kg of body weight per day.

In practice, the therapeutically effective amount may vary depending on numerous factors associated with the treatment subject, including age, weight, height, severity of the disorder, administration technique, and other factors. The therapeutically effective amount of the composition administered to a given subject may be determined by medical personnel taking into account the relevant circumstances.

The composition may be administered as a single dose or as part of a dosage regimen. For a dosage regimen, the therapeutically effective amount is adjustable dose to dose to provide a desired therapeutic response.

In another method aspect, melatonin, resveratrol, EGCG, and vitamin B12 are used in a combinatorial treatment method. The combinatorial treatment includes administering to a human having Alzheimer's disease a therapeutically effective combination of melatonin, resveratrol, EGCG, and vitamin B12. In this method the melatonin, resveratrol, EGCG, and vitamin B12 may be contained in the same composition or they may be administered at different times, but still a suitable time for the patient to receive their combined therapeutic effectiveness.

The "subject" referred to here is preferably a human or animal subject or patient that has been identified as having a condition characterized by amyloid-beta peptide aggregates, including but not limited to Alzheimer's disease.

The term "contacting" refers to placing vitamin B12 in direct physical association with the subject. This is achieved using either a solid, liquid, or gaseous form of a composition comprising vitamin B12. It includes events that take place both intracellularly and extracellularly and may be accomplished by any of the administration techniques set forth above or any other conventional drug administration technique.

The results discussed in the Examples section show that vitamin B12 influences the way that amyloid-beta peptides respond to external stimuli such as electromagnetic radiation. This is because vitamin B12 hinders amyloid-beta peptide monomer self-association into toxic forms, and because vitamin B12 binds directly with the amyloid-beta peptide monomers. Advantageously, vitamin B12's influence on the amyloid-beta peptides can be exploited to provide a diagnostic test for detecting amyloid-beta peptides in a sample containing biological material such as bodily fluid or bodily tissue. Accordingly, another aspect of is a diagnostic test for detecting the presence of amyloid-beta peptides.

A diagnostic test for detecting the presence of amyloid-beta peptides, according to yet another embodiment comprises stimulating a signal from a sample having been exposed to vitamin B12 and identified as being at risk for containing amyloid-beta peptides and detecting the signal. The signal indicates the presence or absence of amyloid-beta peptides in the sample.

The signal is preferably stimulated and detected using a spectroscopic technique such as fluorescence spectroscopy or surface plasmon resonance (SPR) spectroscopy.

When fluorescence spectroscopy is employed, a fluorescence signal from tyrosine, intrinsic to the amyloid-beta peptides, is detectable. The strength of the fluorescence signal is a function of the concentration of vitamin B12 in proximity to the tyrosine on the amyloid-beta peptides. In general, the strength of the tyrosine fluorescence signal tends to decrease with increasing concentration of vitamin B12.

Alternatively, when fluorescence spectroscopy is employed, the fluorescence signal may be stimulated from a fluorophore associated with the sample. Suitable fluorophores include, but are not limited to, benzothiazole dyes such as thioflavin T ("ThT").

Some particular embodiments of this diagnostic test allow for a determination of the degree of aggregation among amyloid-beta peptide monomers in the sample. This is achieved by comparing successively detected fluorescence signals stimulated from the fluorophore. In the fluorescence spectroscopy experiments described in the Examples section, I show that successively detected fluorescence signals from samples of fluorophore-associated amyloid-beta peptide reveal whether, and by what extent, the amyloid-beta peptides have aggregated in the sample.

When SPR spectroscopy is employed, the sample is preferably positioned on a substrate and a solution of vitamin B12 is flowed over the substrate. The SPR detected signal is a function of the degree of binding between vitamin B12 and amyloid-beta peptides in the sample.

EXAMPLES

The embodiments of the invention described above will be even better understood in the context of the following examples. These examples are not intended to limit the scope of the embodiments in any way.

Example 1

Vitamin B12 Binds to Amyloid-Beta Peptide

This section shows that vitamin B12 binds to amyloid-beta peptide.

Preparation of Amyloid-Beta Peptide Samples. Synthetic Aβ(1-40) peptide was purchased from Biopeptide, Inc. at a purity level≥98%. The hydroxocobalamin form of vitamin B12 and Thioflavin T were purchased from Sigma-Aldrich. All other reagents were of analytical grade.

Samples of Aβ(1-40) were reconstituted in phosphate buffer saline (PBS) (137 mM NaCl, 2.7 mM KCl, 10 mM $Na_2HPO_4$, 2 mM $KH_2PO_4$, pH 7.4), except in surface plasmon resonance experiments, as described below. Immediately after reconstitution into PBS, the pH of the solution was adjusted to 10, allowing for solubilization of the peptide. The pH was then readjusted to 7.4, followed by filtration through a 0.22 µm supor membrane filter. Concentrations of Aβ(1-40) were determined using UV-Vis spectroscopy (Cary 300 spectrophotometer, Varian, Inc) and an extinction coefficient of 1,490 $M^{-1}$ $cm^{-1}$ at 280 nm. Aβ(1-40) samples used in fluorescence experiments to examine peptide/B12 binding included freshly prepared, monomeric Aβ species and "aged" Aβ, incubated for seven days and containing high-molecular weight species.

Preparation of Vitamin B12 Samples. Hydroxocobalamin form of the vitamin B12 was dissolved in phosphate buffer saline (PBS), pH 7.4, unless stated otherwise, followed by filtration through a 0.22 µm supor membrane filter. The vitamin B12 samples were used within twenty four hours of preparation, stored protected from light. Concentrations of B12 were determined using UV-Vis spectroscopy (Cary300 spectrophotometer, Varian, Inc) and an extinction coefficient of 4,900 $M^{-1}$ $cm^{-1}$ at 525 nm.

Intrinsic Tyrosine Fluorescence Spectroscopy Experiments on Amyloid-Beta Peptide in the Presence of Vitamin B12. Intrinsic tyrosine fluorescence was measured as previously described by Lakowicz in *Principles of Fluorescence Spectroscopy*. 2 ed. Vol. 1. 2004, New York: Springer. 445-486, which is hereby incorporated by reference in its entirety. Fluorescence emission spectra of the Aβ(1-40) peptide at 50 µM in PBS were recorded at 25° C. using a Cary Eclipse spectrometer equipped with Peltier temperature control (Varian, Inc). All solutions were filtered through 0.22 µm supor membrane filters. Aβ(1-40) samples containing varying amounts of B12 were excited at 265 nm. The emission spectra were collected at 285-370 nm wavelength range, with each spectrum was corrected for buffer contribution. The intensity for each spectrum was normalized to the highest value detected in the absence of vitamin B12 and plotted as a function of the change in fluorescence intensity. The binding constant, $K_D$, was calculated using equation (1) in SigmaPlot 9.0 (Systat Software, Inc.) assuming 1:1 binding stoichiometry.

$$f = \frac{B_{max} * \text{abs}(x)}{K_D + \text{abs}(x)} \quad (1)$$

Static Vs. Dynamic Quenching. All experiments were performed at 25° C., unless otherwise stated. Absorption spectra were recorded using a UV-Vis Cary300 spectrophotometer (Varian, Inc.) Fluorescence spectra were normalized and corrected for wavelength-dependent sensitivity. Dynamic or collisional quenching was investigated using the Stern-Volmer equation:

$$\frac{F_0}{F} = 1 + k_q \tau_0 [Q] = 1 + K_D [Q] \quad (2)$$

where $F_0$ and $F$ are the fluorescence intensities in the absence or presence of the quencher, B12, respectively; $k_q$ is the biomolecular quenching constant; $\tau_0$ is the lifetime of the unquenched tyrosine (3.2 ns) [34], [Q] is the concentration of B12. The Stern-Volmer quenching constant is given by $K_D = k_q \tau_0$.

Surface Plasmon Resonance (SPR) Experiments. The binding of Aβ(1-40) and vitamin B12 was analyzed by SPR using a Biacore T-200 optical biosensor (Biacore/GE Healthcare). The Aβ peptide was immobilized on CM5 sensor chips using amine coupling chemistry [36]. Briefly, the carboxymethyl dextran surface of a CM5 sensor chip was activated with a 1:1 mixture of 0.4 M 1-ethyl-3-(3-dimethylaminopropyl)-carbodiimide (EDC) and 0.1 M N-hydroxysuccinimide (NHS) at 25° C. A peptide surface (400-800 RU) was created by pulsing Aβ in 10 mM sodium acetate at pH 4.5 over the flow cell. The remaining binding sites on the dextran surface were blocked with 1.0 ethanolamine-HCl, pH 8.5. A reference surface was activated and blocked as outlined above.

Binding experiments were carried out using HBS-EP+ running buffer (0.1 M Hepes, 1.5 M NaCl, 30 mM EDTA, 0.05% v/v surfactant P-20, pH 7.4) at 25° C. All components were 0.22 µm-filtered prior to use. For analysis of kinetic constants, varying concentrations of vitamin B12, ranging from 0 to 1000 µM, were injected over the chip surface at 75 µL/min. Each analyte concentration was injected in triplicate. Surface regeneration was achieved with 10 mM glycine, pH 2.5 and 0.05% SDS at a flow rate of 50 µL/min. Data were analyzed using T200 BiaEvaluation 1.0 (Biacore) software and fit to a 1:1 binding model.

Figure 3:
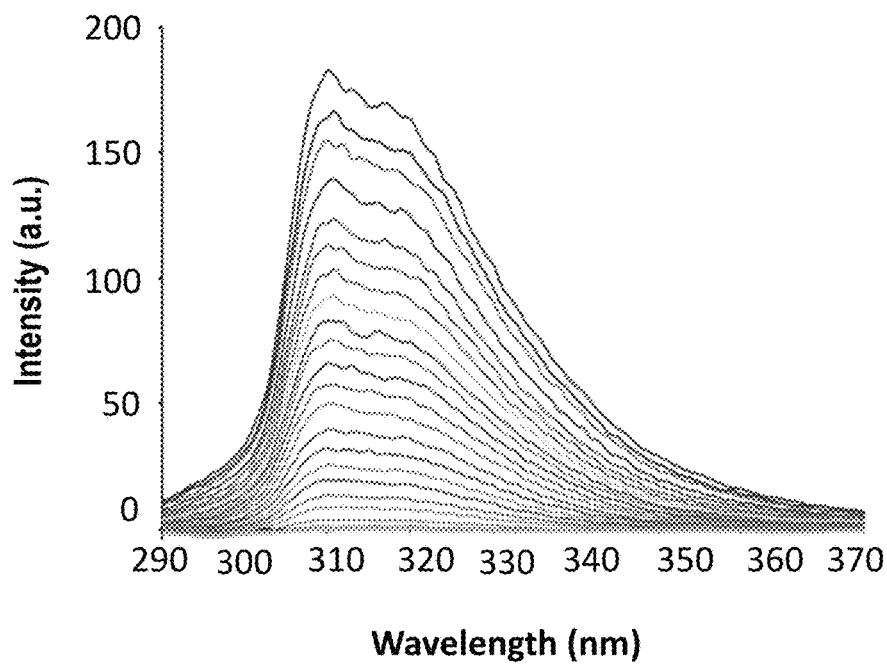
FIG. 3 is a graph showing a plurality of intrinsic tyrosine fluorescence spectra of fresh amyloid-beta peptide in the presence of different concentrations of vitamin B12.
Figure 4:
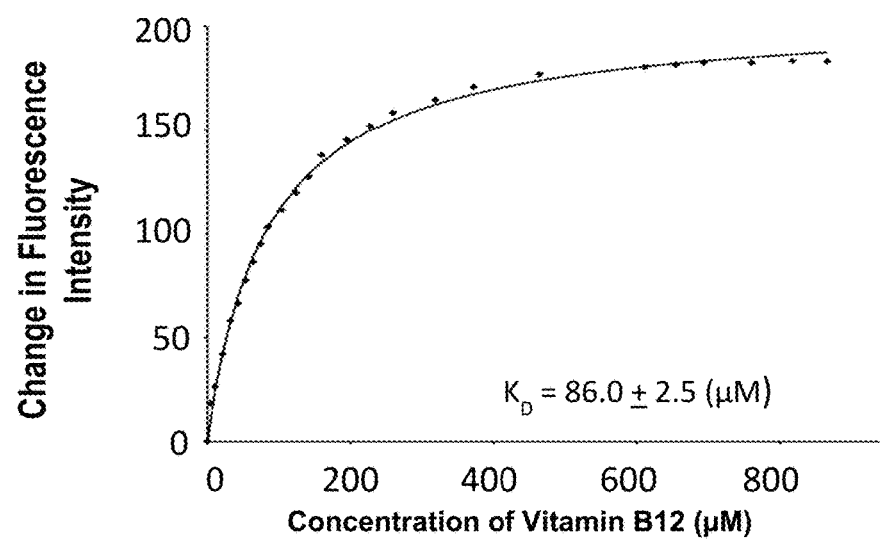
FIG. 4 is a graph of the change in the fluorescence intensity of the data in FIG. 3 as a function of the concentration of vitamin B12.

Results. Binding of B12 to the Aβ peptide was demonstrated using fluorescence and surface plasmon resonance (SPR). Fluorescence experiments were carried out by measuring changes in the emission signal of Aβ(1-40), with its tyrosine residue serving as an intrinsic probe (Ex=265 nm). Vitamin B12 was titrated stepwise into the freshly prepared and aged Aβ(1-40) samples, respectively (FIGS. 3 and 4), providing a way calculate the binding constants and to identify any differences in vitamin B12's affinity for the monomeric (freshly prepared) and self-associated (aged, or higher-order) Aβ forms.

Figure 5:
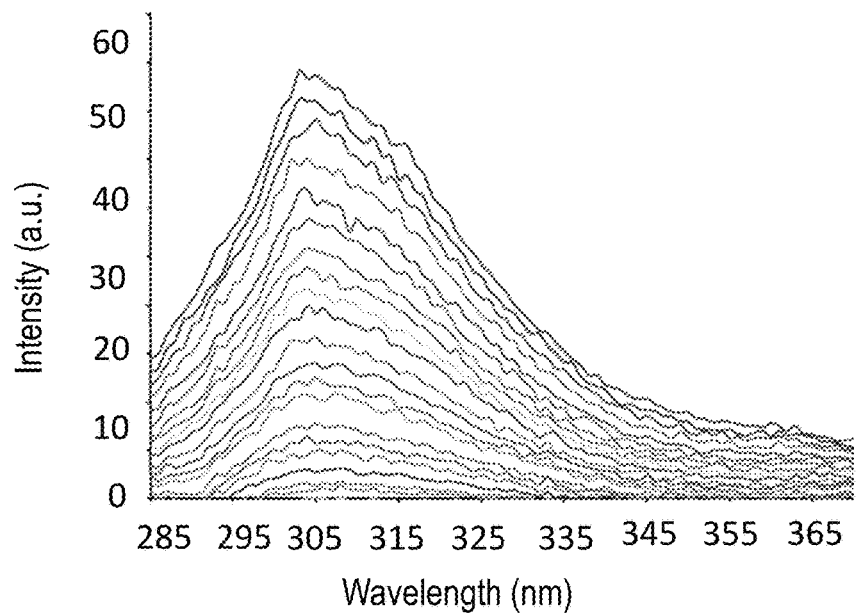
FIG. 5 is a graph showing a plurality of intrinsic tyrosine fluorescence spectra of aged amyloid-beta peptide in the presence of different concentrations of vitamin B12.
Figure 6:
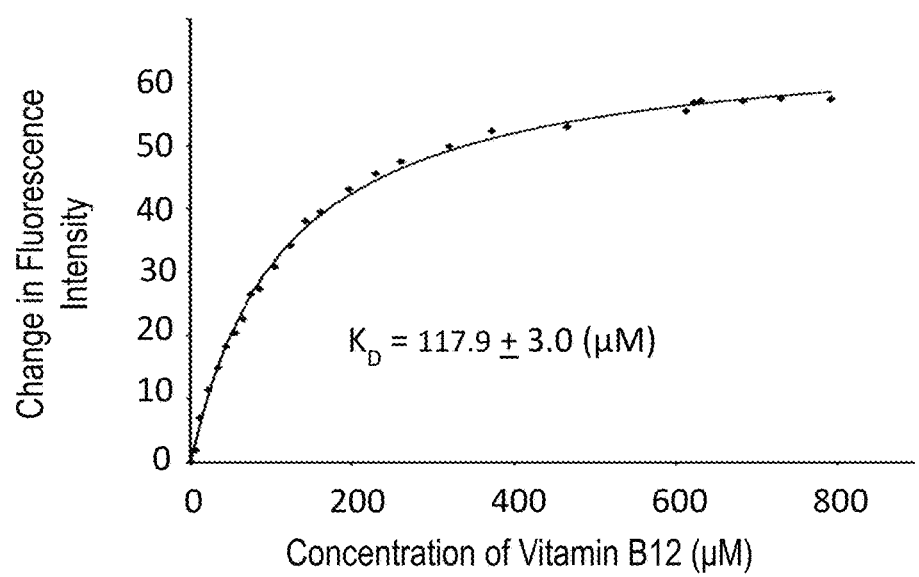
FIG. 6 is a graph of the change in the fluorescence intensity of the data in FIG. 5 as a function of the concentration of vitamin B12.

In FIGS. 5 and 6 the change in fluorescence signal at 305 nm (signal max) upon addition of vitamin B12 is plotted as a function of varying B12 concentration. The resulting binding constants were 87.0±2.7 µM for monomeric and 96.1±3.5 µM for self-associated Aβ peptide.

These results were corroborated by surface plasmon resonance experiments, the results of which are shown in FIGS. 7 and 8. In the SPR experiments, freshly prepared Aβ(1-40) was immobilized on a chip. Subsequently, several solutions containing different concentrations of B12 were passed over the immobilized Aβ(1-40). Referring to FIG. 7, a concentration dependent change in the refractive index at the surface of the chip was detected. This change, reflective of the Aβ peptide/B12 interaction, was monitored in real time. The resulting sensorgrams of FIG. 7 were fit to obtain a binding constant of 131.5 µM. The results of the best-fit are shown in FIG. 8. Collectively, the fluorescence and SPR data demonstrated a direct interaction of B12 with the amyloid-beta peptide. The fact that the binding affinity is on a micromolar scale means that this effect is physiologically relevant.

Example 2

Vitamin B12 Dissociates Higher-Order Amyloid-Beta Peptide Forms and Reduces Self-Association of Amyloid-Beta Peptide Monomers This section shows that vitamin B12 actually dissociates amyloid-beta peptide monomer from higher-order amyloid-beta peptide structures such as oligomers and fibrils.

Thioflavin T Fluorescence Spectroscopy Experiments on Amyloid-Beta Peptide in the Presence of Vitamin B12. The Fluorescence signal was measured as previously described using a Biotek Flx800 fluorescence microplate reader. Aβ(1-

40) peptide samples (30 µM) were incubated at 37° C. in the presence or absence of B12. Following incubation, ThT was added to a final concentration of 10 µM as a probe for fibril formation by Aβ(1-40). All fluoresce readings were corrected for 10 mM sodium phosphate buffer contribution. Thioflavin T (ThT) (Sigma Aldrich) was reconstituted in Nanopure water, aliquoted, and stored at −20° C. Concentration of ThT was determined using UV-Vis spectroscopy (Cary300 spectrophotometer, Varian, Inc) and an extinction coefficient of 36,000 $M^{-1}$ $cm^{-1}$ at 412 nm.

Results. The formation of the higher order amyloid forms by the Aβ(1-40) peptide was monitored using Thioflavin T ("ThT") fluorescence. These results are shown in FIGS. 9 and 10. In the absence of vitamin B12, the Aβ(1-40) formed higher-order aggregates, or fibrils, with a lag phase of approximately 8 hours. Addition of B12 to these aggregates resulted in a reduction of the ThT fluorescence, indicating fibril dissociation. Importantly, in the presence of vitamin B12, there was no increase in the ThT fluorescence signal, indicating that vitamin B12 reduces self-association of the amyloid-beta peptide.

Example 3

Vitamin B12 Prevents Amyloid-Beta Peptide Induced Cell Death in Hippocampal Cells This section shows that vitamin B12 protects hippocampal cells by preventing amyloid-beta peptide from forming toxic oligomers.

Neuronal Cell Culture Experiments. Neuronal cell culture experiments were conducted using methodologies described previously by Lee, et al in *Cell*, Vol. 111(2), pages 219-230 (2002); Lei, et al in *EMBO J*, Vol. 21(12), pages 2977-2989 (2002); Xin, et al in *J Neurosci, Vol.* 25(1), pages 139-48 (2005); and Xin, et al in *European Journal of Neuroscience*, Vol. 21(3), pages 622-636 (2005).

Briefly, hippocampal tissue was dissected from Wistar rat embryos (18 days gestation or E18) at 4° C. Dissociated hippocampal neurons were plated at a density of approximately $2.0 \times 10^4$ cells/cm$^2$ onto 35 mm culture dishes coated with poly-D-lysine. Neurons were matured in culture for 21 days in vitro in NEUROBASAL® media (Invitrogen) supplemented with B27 (2%), bFGF2 (2 ng/mL) and L-glutamine (0.5 mM). The Aβ(1-40) was dissolved in DMSO, followed by dilution into culture medium (final DMSO concentration was 1%), and incubation at 37° C. for three days to form Aβ(1-40) oligomeric species. This pre-aggregated Aβ was added to the culture medium at a final concentration of 25 µM on the 21$^{st}$ day in vitro (DIV 21), a concentration that has been previously established to cause neurotoxicity without causing overt neuronal death in hippocampal cell culture. Some pre-aggregated Aβ samples were incubated with varying dosages of B12 (50, 25, or 12.5 µM final concentration). All cells were incubated for 72 hours. Cell culture medium containing 1% DMSO was used as a vehicle control to demonstrate that DMSO neither prevented nor accelerated neuronal cell death.

Trypan Blue Staining and Cell Counting. Following the three-day incubation, Trypan Blue staining of dead neuronal cells was performed by removing 1 mL of medium from each dish and adding 50 µL of Trypan Blue (0.2%) (Harleco EMD). The dishes were gently mixed for two minutes prior to removal of all solution. Five random fields, one from each corner and one from the center of the dish, were counted for both live and dead cells at 63× magnification to obtain a percentage of cell death. Mann-Whitney U statistical analyses were performed using NCSS 2000 (NCSS, LLC) software. Following counting, a representative picture of each dish was taken.

The physiological relevance of the B12/Aβ interaction was evaluated using neuronal cell culture experiments. Because the hippocampus is the first region of the brain to be affected by the Alzheimer's pathology, these experiments focused specifically on this region. The amyloid-beta peptide was incubated for 3 days prior to addition to hippocampal cell culture to generate higher-order species demonstrated to be toxic by others.

Figure 11:
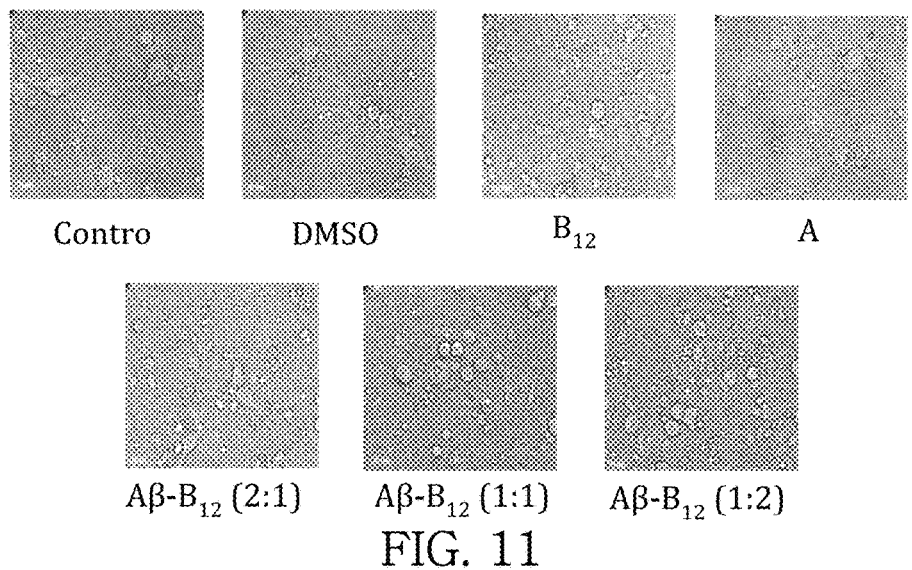
FIG. 11 is a series of micrographs of the samples indicated.
Figure 12:
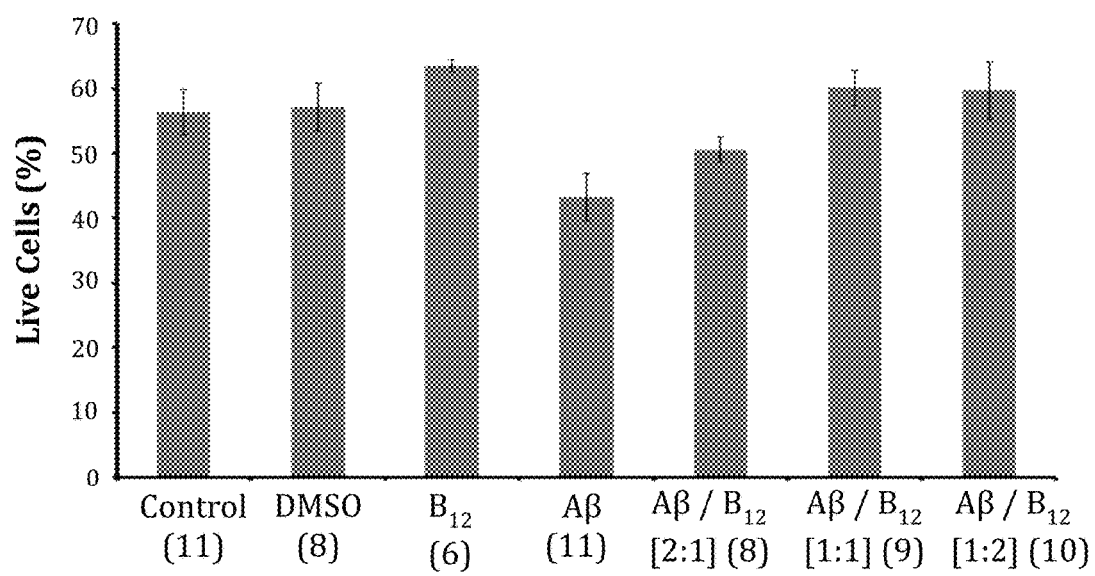
FIG. 12 is bar graph showing the quantification of cell death counts for the samples represented in FIG. 11, in which the numbers in parenthesis reflect the number of trials and the numbers in brackets represent the Aβ:B12 ratio.

Referring to FIG. 11, it is notable, that addition of freshly prepared Aβ peptide to the hippocampal cell culture did not cause neuronal cell death. As depicted in FIG. 12, neuronal cell death is observed upon addition of the amyloid-beta peptide. Importantly, this effect is alleviated in the presence of B12, demonstrating its neuroprotective efficacy.

Example 4

A Combination of B12, Resveratrol, Melatonin, and EGCG is Effective Against Factors of Alzheimer's Disease This section shows that B12, resveratrol, melatonin, and EGCG, when combined, are effective against factors associated with causing Alzheimer's disease.

A combinatorial approach was used to test the efficacy of the four compounds at reducing Alzheimer's disease pathology in a cell culture model system. The goal was to determine which combinations of the compounds provide the highest effectiveness.

A mouse N2a neuroblastoma cell line transfected with human APPswe is a well-established cell culture model of Alzheimer's disease, so it was employed in these studies. The cells were treated with different combinations of the four active ingredients. The combinations tested on the cell culture were:

B12 (B) alone;
resveratrol (R) alone;
melatonin (M) alone;
EGCG (E) alone;
resveratrol+EGCG+melatonin (REM);
resveratrol+EGCG+B12 (REB);
resveratrol+melatonin+B12 (RMB);
EGCG+melatonin+B12 (EMB); and
B12+resveratrol+EGCG+melatonin (BREM).

The biomarkers for Alzheimer's disease that were measured and the technique used to measure them are shown in Table 1.

TABLE 1

Alzheimer's Disease Biomarkers and Associated Measurement Technique

| BIOMARKER | MEASUREMENT TECHNIQUE |
|---|---|
| Toxic amyloid-β peptides 40 and 42 | ELISA |
| Cell survival promoting proteins: BCL-2 and BCL-XL | Western Blot |
| APP processing: Bace1, ADAM-10 | Western Blot |
| Inflammation: IL-6, TGF-β1 | ELISA |
| Oxidation: catalase, SOD1, GPx-1 | Western Blot |
| Reactive oxygen species | H2DCFDA Assay |

Results

Figure 13:
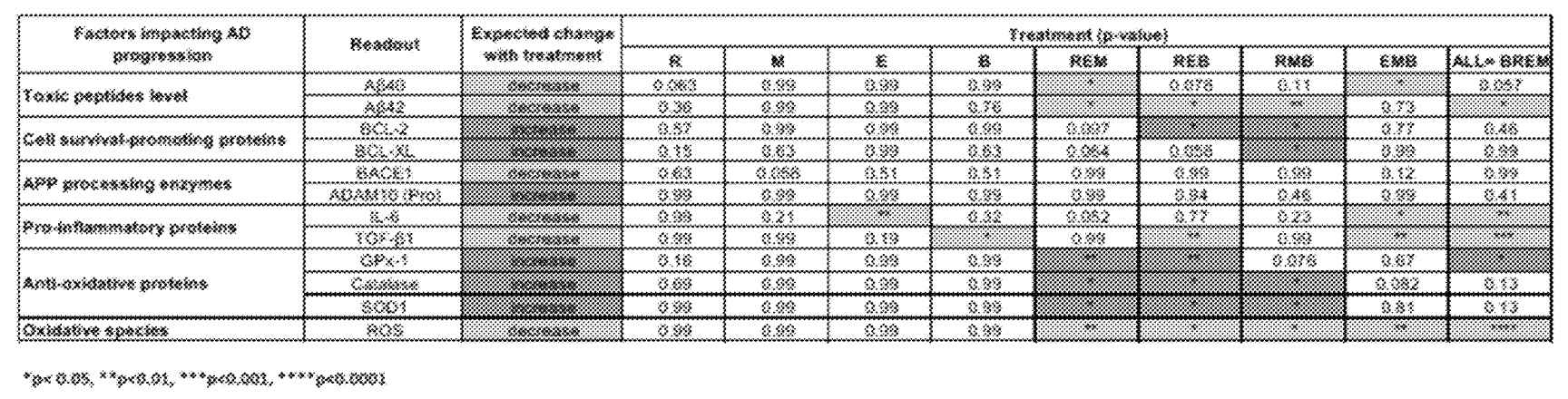

The results of these experiments are summarized in the table of FIG. 13. Each of the combinations was tested against each of the biomarkers, which are labeled "readout." The result, in terms of whether an increase or decrease in the readout was expected, for each treatment is indicated in the third column from the left.

The numbers in the table are statistical p-values. The statistically significant p-values are shaded with *$p<0.05$, $p<0.01$, *$p<0.001$, ****$p<0.0001$. The numbers represent the p-values for the results that were not statistically significant.

The results show that the result of combining B12, resveratrol, EGCG, and melatonin is not necessarily predictable. This is probably because Alzheimer's pathology is based on a complex topology of signaling networks and biochemical pathways. Certain combinations of these ingredients seem to be antagonistic. Based on the overall trends, the BREM composition containing B12, resveratrol, EGCG, and melatonin performed the most favorably. This could not have been expected based on the test results from the individual compounds or the other combinations that were tested.

Experimental Details

Small Compounds/Reagents: Vitamin B12 was purchased from Sigma-Aldrich. Melatonin, (−)-epigallocatechin gallate (EGCG), and trans-resveratrol were purchased from Cayman Chemical. All compounds were of =98% purity. All other reagents were ACS or histological grade.

Compound solubilization/treatment: Each of the 3 compounds: resveratrol (R), melatonin (M) and EGCG (E) were stored in a desiccator at −20 C and vitamin B12 (B) was stored at 4 C. All compounds were made fresh and re-suspended immediately prior to use, to avoid potential degradation. R, M and E were dissolved in 100% ethanol to a stock concentration of 100 mM, whereas B was dissolved in supplemented DMEM to a stock concentration of 10 mM. Each compound was subsequently diluted with supplemented DMEM to 10 μM (R), 30 μM (M), 20 μM (E) and 40 μM (B) and used in 12-hour cell treatments (individually or in combinations).

Cell culture: N2A cells containing the Swedish mutation (N2A/APPswe), were maintained in high glucose DMEM medium (Gibco) supplemented with 10% FBS (Atlanta Biologicals), 100 U/mL penicillin/streptomycin (Gibco) and 0.2 mg/mL G418 (Life Technologies), and kept in a hydrated, 5% $CO_2$ environment at 37° C. They were cultured in T75 flasks (Nunc).

Cells were passaged every 3-4 days, at approximately 80% confluence. The medium was removed and cells were carefully washed with phosphate buffered saline (PBS) (Gibco). The PBS was removed and 1 mL 0.25% Trypsin-EDTA (Gibco) was added to dissociate the cells. The cells were placed at 37 C for 2 minutes, until the cells detached.

Ten mL of fresh, supplemented DMEM was added to the trypsin treated cells, collected and transferred to a 50 mL Falcon tube (BD). Cells were centrifuged for 5 minutes at 190 g, to pellet the cells and remove the trypsin. The medium was removed and the cells were re-suspended in 10 mL of supplemented DMEM.

Cells were sub-cultured into dishes or plates appropriate for the pending experiment. Twenty percent of the cells were added back to new T75 flasks for further growth.

Western Blots: N2A Swedish cells were seeded (described above) into ten 6 cm2 dishes, approximately 2.2×106 cells in each dish. Forty eight hours later cells were treated with the compounds in 4 mL of supplemented DMEM, as indicated, and placed at 37 C, 5% $CO_2$.

The cells were placed on ice and the medium was removed. The cells were carefully washed once with ice cold PBS and harvested, with a cell scraper, in 1.5 mL ice-cold PBS. The cells were centrifuged for 5 minutes at 1500 g at 4 C. The PBS was removed and cell pellet immediately frozen on dry ice and stored at −80 C.

In order to extract the protein, the cell pellets were homogenized with a Kontes Pellet Pestle in 70 μL extraction buffer [46]: 120 mM NaCl, 20 mM HEPES pH 7.4, 0.1% Triton X-100, 3 mM Sodium β-glycerophosphate, 1 mM dithiothreitol (DTT), 1 protease tablet (Thermo Scientific) and 1 mM phenylmethanesulfonyl fluoride (PMSF) added just prior to use.

Homogenized pellets were centrifuged for 5 minutes at 12,000 g at 4 C. The supernatant was removed and added to 70 μl 2× sample buffer: 100 mM Tris pH 6.8, 4% SDS, 20% glycerol, 5% mercaptoethanol, 5 mM EDTA pH 8, 0.1 mg/mL bromophenol blue, and boiled at 95° C. for 3 minutes. The preparations were briefly centrifuged, and loaded onto an SDS PAGE gel.

Gels were ran at 180V for 1 hour in 1× running buffer: 125 mM Tris, 200 mM glycine and 0.1% SDS. Gels were subsequently transferred to nitrocellulose membrane using a semi-dry transfer method (BioRad), at 23V for 26 minutes. The transfer buffer was 125 mM Tris, 200 mM glycine, 20% methanol and 0.04% SDS. Membranes were stained with Ponceau S stain and washed with Tris-buffered saline, Tween-20 (TEST) (500 mM Tris pH 7.4, 1.5M NaCl and 0.05% Tween20). Membranes were blocked with Odyssey blocking buffer (LI-COR) at room temperature for 30 minutes prior to antibody incubation.

The membranes were incubated with the primary antibody for 2 hours at room temperature, with shaking. The primary antibodies used included: anti-Catalase, Sigma (mouse); anti-glutathione peroxidase I (GPX1), Thermo Fisher (rabbit); anti-superoxide dismutase (SOD1), (rabbit); anti-BCL-2, Cell Signaling (50E3, rabbit); anti-BCL-XL, Cell Signaling (54H6, rabbit); anti-ADAM10, Millipore (rabbit); anti-actin, Sigma (A2066, rabbit).

Each membrane was washed in TEST 3×5 minutes and the respective secondary antibody was added for 1 hour at room temperature, with shaking: Goat anti-rabbit IRDye 800CW, or donkey anti-mouse IRDye 680LT (LI-COR). Membranes were washed in TEST 5×5 minutes, and imaged using the Odyssey infra-red imaging system (LI-COR). Quantification was performed using the Odyssey application software version 3.0 (LI-COR).

ELISAs: N2A/APPswe cells were seeded into 24-well plates (Nunc) as previously described at a density of approximately 0.05×106 cells per well. Forty eight hours later cells were treated with the compounds in 300 μL of supplemented DMEM, as indicated, and placed at 37 C, 5% $CO_2$.

Twelve hours later the medium was removed and split into 4 separate tubes (2×100 μL and 2×50 μL). The medium was placed immediately on dry ice and stored at −80° C. until use. For the Aβ40 and Aβ42 a mouse specific kit (Invitrogen) was used and the assay carried out according the manufactures' instructions, but using the supplemented DMEM for sample and standard dilutions. Briefly, Aβ40 samples were diluted 1:50 in supplemented DMEM and Aβ42 samples were diluted 1:10.

Respective detection antibodies were added to all standards and samples, which were incubated at room temperature for 3 hours, with gentle shaking. A well was left empty for the chromogen blank control. After the incubation all wells were washed 3 times with wash solution (provided) and the respective HPR-tagged secondary antibody was added, diluted in the antibody diluent (provided). This was allowed to sit at room temperature for 30 minutes. The chromogen blank was left empty. The wells were again washed and the chromogen solution was added to all wells and incubated for 20 minutes, in the dark. The reaction was stopped with the stop solution provided.

The plates were immediately assayed for absorbance at 450 nm. Total mouse Tau was assayed using a mouse specific kit (Invitrogen), according to the manufactures' instructions. Briefly, cells were seeded, treated and harvested as for the Western blots, described above. The frozen cell pellets were homogenized in extraction buffer and centrifuged for 5 minutes at 12000 g at 4° C. The supernatant was diluted 1:10 in standard diluent buffer (provided), in 96-well plates (provided) and incubated at room temperature for 2 hours. A well was left empty for the chromogen blank control. The wells were washed with the wash buffer (provided) and detection antibody (provided) was added, and incubated for 1 hour at room temperature.

Wells were washed and HPR-tagged secondary antibody was added, diluted in the antibody diluent (provided). This was allowed to sit at room temperature for 30 minutes. The chromogen blank was left empty. The wells were again washed and the chromogen solution was added to all wells and incubated for 20 minutes, in the dark. The reaction was stopped with the stop solution provided. The plates were immediately assayed for absorbance at 450 nm.

IL-6 and TGFβ1 were assayed in a similar way according the manufactures' instructions, using mouse ELISA kits (Affymetrix, eBiosciences), but TGFβ1 samples were first activated with 1M HCl for 10 minutes, followed by 1M NaOH to neutralize the acid. 96-well plates (provided) were coated with the respective capture antibody, overnight at 4° C. Plates were washed with 1×PBS, 0.05% Tween-20 and then blocked ELISA diluent (provided) for 1 hour. Plates were washed and standards/samples were diluted in supplemented DMEM. IL-6 samples were added undiluted and TGFβ1 samples were diluted 1:10. The plates were incubated at room temperature for 2 hours without shaking.

Plates were washed and the respective detection antibody was added, diluted in 1×ELISA diluent (provided) and incubated for 1 hour at room temperature. Plates were washed and Avidin-HPR, diluted in 1×ELISA diluent, was added to each well. Plates were incubated for 30 minutes at room temperature. Plates were washed and 1×TMBs solution (provided) was added. The plates were incubated for 15 minutes, in the dark, and the reaction stopped with 1M H3PO4. The plates were immediately assayed for absorbance at 450 nm.

Quantification of Reactive Oxygen Species: N2A Swedish cells were seeded, as above, into a clear-bottom black-coated 96-well plate (Nunc), at approximately $0.0125 \times 10^6$ cells per well. Forty eight hours later cells were treated with the compounds in 50 μL of supplemented DMEM, as indicated, and placed at 37 C, 5% $CO_2$. Twelve hours later the medium was removed and replaced with phenol-red free DMEM without any supplements, but including 25 μM 2',7'-dichlorodihydrofluorescein diacetate (ATT Bioquest). The cells were returned to 37 C, 5% $CO_2$ for 30 minutes then washed once with PBS and fresh supplement free phenol-red free DMEM was added. Cells were immediately analyzed for fluorescence emission using excitation at 485 nm and emission at 528 nm.

Statistical analysis: The data were analyzed using a Kruskal-Wallis test, followed by Dunn's multiple comparison test, and compared to the control (*$p<0.05$, $p<0.01$, *$p<0.001$, ****$p<0.0001$). GraphPad Prism® software was used for all analyses.

Unless otherwise defined, all technical and scientific terms used herein are intended to have the same meaning as commonly understood in the art to which this disclosure pertains at the time of its filing. Although various methods and materials similar or equivalent to those described can be used in the practice or testing of the embodiments, suitable methods and materials are described. The skilled should understand that the methods and materials used and described are examples and may not be the only ones suitable for use.

The embodiments have been described in some detail, but it will be apparent that various modifications and changes can be made within the spirit and scope of the embodiments as described in the foregoing specification.

That which is claimed is:

1. A method of treating Alzheimer's disease, the method comprising administering to a human having Alzheimer's disease a therapeutically effective amount of a pharmaceutically acceptable transdermal dosage form by applying the dosage form to the human's skin, the dosage form including an active ingredient combination consisting of melatonin, resveratrol, EGCG, and vitamin B12.

2. The method of claim 1, wherein the dosage form comprises a liquid solution of the active ingredient combination consisting of melatonin, resveratrol, EGCG, and vitamin B12.

3. A combinatorial treatment method for Alzheimer's disease, the combinatorial treatment method comprising administering to a human having Alzheimer's disease a therapeutically effective amount of a transdermal spray pharmaceutical dosage form including an active ingredient combination consisting of melatonin, resveratrol, EGCG, and vitamin B12 by spraying the dosage form onto the human's skin.

4. The method of claim 3, wherein the dosage form comprises a liquid solution of the active ingredient combination consisting of melatonin, resveratrol, EGCG, and vitamin B12.

5. The method of claim 1, wherein the combination of melatonin, resveratrol, EGCG, and vitamin B12 in the pharmaceutical dosage form is more effective against an Alzheimer's pathology than melatonin, resveratrol, EGCG, and vitamin B12 are individually against the Alzheimer's pathology.

6. The method of claim 3, wherein the combination of melatonin, resveratrol, EGCG, and vitamin B12 is more effective against an Alzheimer's pathology than melatonin, resveratrol, EGCG, and vitamin B12 are individually against the Alzheimer's pathology.

* * * * *

SEQUENCE LISTING

```
<160> NUMBER OF SEQ ID NOS: 1

<210> SEQ ID NO 1
<211> LENGTH: 42
<212> TYPE: PRT
<213> ORGANISM: Homo sapiens

<400> SEQUENCE: 1

Asp Ala Glu Phe Gly His Asp Ser Gly Phe Glu Val Arg His Gln Lys
1               5                   10                  15

Leu Val Phe Phe Ala Glu Asp Val Gly Ser Lys Lys Gly Ala Ile Ile
            20                  25                  30

Gly Leu Met Val Gly Gly Val Val Ile Ala
        35                  40
```